(12) United States Patent
Flament et al.

(10) Patent No.: US 6,511,838 B1
(45) Date of Patent: Jan. 28, 2003

(54) GENES CODING FOR β-AGARASES AND THEIR USE FOR PRODUCING AGAR BIODEGRADATION ENZYMES

(75) Inventors: Didier Flament, Roscoff (FR); Tristan Barbeyron, Cleder (FR); Jean-Claude Yvin, Saint Malo (FR); Philippe Potin, Roscoff (FR); Bernard Kloareg, Plouenan (FR)

(73) Assignee: Laboratoires Goemar S.A., Saint Malo (FR)

( * ) Notice: Subject to any disclaimer, the term of this patent is extended or adjusted under 35 U.S.C. 154(b) by 0 days.

(21) Appl. No.: 09/719,402

(22) PCT Filed: Jun. 11, 1999

(86) PCT No.: PCT/FR99/01397

§ 371 (c)(1),
(2), (4) Date: Dec. 12, 2000

(87) PCT Pub. No.: WO99/66052

PCT Pub. Date: Dec. 23, 1999

(30) Foreign Application Priority Data

Jun. 12, 1998 (FR) .............................. 98 07419

(51) Int. Cl.[7] .............................. C12N 9/00; C12N 9/24; C12N 9/38; C12N 9/42; C12N 1/20; C12N 15/00

(52) U.S. Cl. ........................ 435/209; 435/183; 435/200; 435/207; 435/252.3; 435/252.33; 435/320.1; 536/23.2; 536/23.74

(58) Field of Search ................................. 435/183, 200, 435/207, 209, 252.33, 320.1, 252.3; 536/23.2, 23.74

Primary Examiner—Rebecca E. Prouty
Assistant Examiner—Manjunath N. Rao
(74) Attorney, Agent, or Firm—Antonelli, Terry, Stout & Kraus, LLP

(57) ABSTRACT

The invention relates to the novel *Cytophaga drobachiensis* strain deposited in the DSMZ Collection (Deutsche Sammlung von Mikroorganismen und Zellkulturen GmbH (German Collection of Microorganisms and Cell Cultures)) on May 8, 1998 under the number DSM 12170, the agaA gene coding for a β-agarase and having SEQ ID No. 1, the agaB gene coding for a β-agarase and having SEQ ID No. 3, said genes coding for a β-agarase of *Cytophaga drobachiensis* DSM 12170, and the specific nucleic acid sequence of the agaA gene coding for a specific peptide fragment AgaA' which has conserved β-agarase activity, and having SEQ ID No. 5, as well as the protein AgaA of *C. drobachiensis* DSM 12170 having SEQ ID No. 2, the protein AgaB of *C. drobachiensis* DSM 12170 having SEQ ID No. 4 and said peptide fragment AgaA' of *C. drobachiensis* DSM 12170 having SEQ ID No. 6.

17 Claims, 12 Drawing Sheets

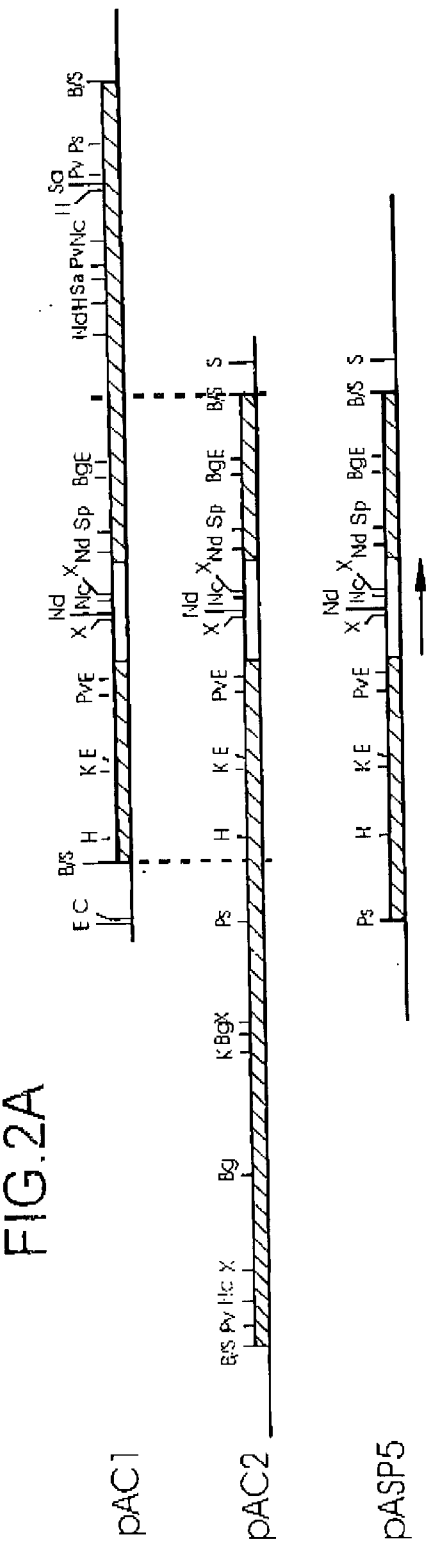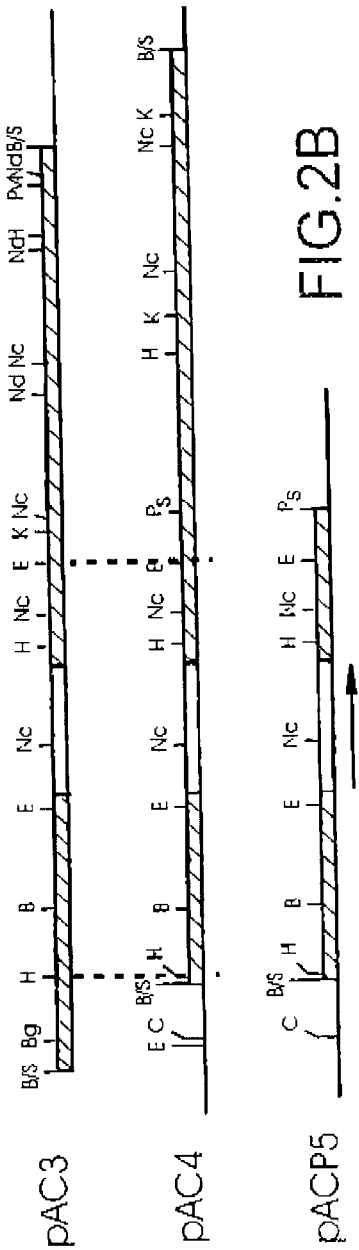

FIG.3A

```
TTATTCTTACTAATATTGTAGGAAAAATTTAACACAAAAAAACATCTTTGTTCAGTTTTGT    60

CGAGTGGTAAAACCTAGAAAACAGACACGGCATTGTATATTTGGCGATGATTCATCTGT    120
          -35                                    -10
                                                agaA
TTGTTTGTTGAATACATTTTATTAACCCTAAAATTACATTATCATGAAAAAAAATTAT      180
                                           fM  K  K  N  Y      5
       EcoRI
CTTTTACTGTATTTTATTTTCTTTGTGTGGCTCTATCGCTGCACAGGACTGGAACGGA     240
 L  L  Y  F  I  F  L  L  C  G  S  I  A  A  Q  D  W  N  G       25

ATTCCTGTACCTGCCAATCCCGGAAATGGTATGACTTGGCAATTACAGGATAATGTTTCG   300
 I  P  V  P  A  N  P  G  N  G  M  T  W  Q  L  Q  D  N  V  S    45

GATAGTTTTAATTACACAAGTAGTGAAGGAAATAGGCCTACTGCCTTTACTAGTAAATGG   360
 D  S  F  N  Y  T  S  S  E  G  N  R  P  T  A  F  T  S  K  W    65

AAACCTTCCTATATCAATGGATGACTGGTCTGATCAACAATTTTAATGCCGCCCAG       420
 K  P  S  Y  I  N  G  W  T  G  P  G  S  T  I  F  N  A  A  Q    85

GCATGGACCAATGGTTCTCAATTGGCAATTCAGGCACAACCAGCAGGAATGGAAAATCT    480
 A  W  T  N  G  S  Q  L  A  I  Q  A  Q  P  P  A  G  N  G  K  S  105

TACAACGGAATTATCACCTCCAAAATAAGATCCAGTACCCGGTGTATATGGAAATTAAG   540
 Y  N  G  I  I  T  S  K  N  K  I  Q  Y  P  V  Y  M  E  I  K    125

GCCAAGATAATGGACCAGGTACTAGCAAATGCTTTCTGGACCTTGACTGACGACGAGACT   600
 A  K  I  M  D  Q  V  L  A  N  A  F  W  T  L  T  D  D  E  T    145

CAGGAAATTGATATTATGGAAGGCTATGGCAGTGATCGGGGGGGAACTTGGTTCGCCCAA   660
 Q  E  I  D  I  M  E  G  Y  G  S  D  R  G  G  T  W  F  A  Q    165

AGAATGCATTTGAGCCACCATACATTTATTCGTAACCCCTTTACGGATTATCAGCCTATG   720
 R  M  H  L  S  H  H  T  F  I  R  N  P  F  T  D  Y  Q  P  M    185
```

FIG.3A (CONTINUATION)

```
                NcoI
GGAGACGCTACATGGTATTACAACGGAGGTACACCATGGCGTTCAGCATATCACCGTTAT    780
 G  D  A  T  W  Y  Y  N  G  G  T  P  W  R  S  A  Y  H  R  Y    205

GGATGTTATTGGAAAGATCCATTTACATTGGAATATTATTGACGGGGTAAAGGTTAGA      840
 G  C  Y  W  K  D  P  F  T  L  E  Y  Y  I  D  G  V  K  V  R    225

ACGGTTCACAAGAGCCGAAATGATCCTAATAATCATCTCGGCGGAACAGGGTTGAATCAG    900
 T  V  T  R  A  E  I  D  P  N  N  H  L  G  G  T  G  L  N  Q    245

GCAACAAATATTATTGATTGTGAAAATCAAACAGATTGGAGGCCCGGCTACTCAA         960
 A  T  N  I  I  D  C  E  N  Q  T  D  W  R  P  A  A  T  Q       265

GAAGAACTGGCCGATGATAGCAAAAATATCTTCTGGGTCGATTGGATACGTGTGTACAAG    1020
 E  E  L  A  D  D  S  K  N  I  F  W  V  D  W  I  R  V  Y  K    285

CCTGTTGCCGGTAAGTGGAGGTGGAAACAACGACGGTGCCACTGAATTTCAATAT         1080
 P  V  A  V  S  G  G  G  N  N  D  G  A  T  E  F  Q  Y          305

GATTTAGGAACGGACACCTCGGCTGTGTGGCCAGGGTATACACGGGTTCCAACACCACT    1140
 D  L  G  T  D  T  S  A  V  W  P  G  Y  T  R  V  S  N  T  T    325

AGGGCTGGTAATTTGGATGGCGAACACCAATGACATCGGATCAAGAGATCGTGGGGCT    1200
 R  A  G  N  F  G  W  A  N  T  N  D  I  G  S  R  D  R  G  A    345

TCTAACGGAAGGAACAATATAAACCGTGATATTAATTTTAGTTCAAACTAGGTTCTTC    1260
 S  N  G  R  N  N  I  N  R  D  I  N  F  S  S  Q  T  R  F  F    365

ACTCAAGACCTATCCAATGGCACTTATAACGTATTGATCACTTTTGGGACACCTATGCC    1320
 T  Q  D  L  S  N  G  T  Y  N  V  L  I  T  F  G  D  T  Y  A    385

CGAAAAAATATGAACGTCGCGGCCGAAGGGCAAAATAAATTAACAAACATAAACACCAAT   1380
 R  K  N  M  N  V  A  A  E  G  Q  N  K  L  T  N  I  N  T  N    405
```

```
GCCGGGCAATATGTTAGTAGGTCGTTTGACGTAAATGTCAACGACGGAAAACTAGATTTG   1440
 A  G  Q  Y  V  S  R  S  F  D  V  N  V  N  D  G  K  L  D  L    425

CGATTTCAGTTGGTAATGGCGGGGATGTGTGGTCCATTACAAGAATCTGATTAGAAAA     1500
 R  F  S  V  G  N  G  G  D  V  W  S  I  T  R  I  W  I  R  K    445

GTTACGAGCAACAGGCTAATTGTTAGCGGCAAAAGGATTAACATTGGAAGATCCTGTG     1560
 V  T  S  N  A  N  L  L  A  A  K  G  L  T  L  E  D  P  V      465

GAAACTACGGAATTTTTATATCCTAACCCGCAAAAACAGATGATTTGTGACTGTTCCC     1620
 E  T  T  E  F  L  Y  P  N  P  A  K  T  D  D  F  V  T  V  P    485

AATAGTGAAATTGGAAGTAGTATAATCATCTATAATAGTGCAGGTCAAGTAGTGAAAAAA   1680
 N  S  E  I  G  S  S  I  I  I  Y  N  S  A  G  Q  V  V  K  K    505

GTAAGTGTGGTTTCCGAAAATCAGAAAACTTATGTCCTAAAGGAATTGCTAAAGGAATGTAC 1740
 V  S  V  V  S  E  N  Q  K  I  S  L  E  G  F  A  R  K  G  M  Y 525

TTTATCAATTTGAATGGTCAGAGTACAAAACTTATTGTCCAATAACACAATAACAATT    1800
 F  I  N  L  N  G  Q  S  T  K  L  I  V  Q  Ter               539

CAATTAAACGACAAAGGCGCTCGATGATACAGAAAGGCCCTTTGTCGTTTTTAAGTTAC    1860

TTCAGGAACCAAGATAAATTTTAGGTGGTATTGTTAGCTTCTCTCTAACTAGAATATGAT   1920

CTGTGTTTTGCGGGCTTCTTGTACTTGCTGTAACCGCTTCGTTTTTGTGCAATGTCGGCA   1980

CATGGTGTATGCCCTGTTTACTGGGTAAATTAGGTACTTTTCTTTTTGAAGCTTA
```

FIG. 3A (CONTINUATION)

FIG.3B

```
GTCTTTATCACAATTCTATCTTAGAATTCTTACTAATGCTGACAAAACTACGGCTGCAAC                    60

CGTGTATTACGATAACTTCTCTATCATTGAAAAAGAAGAGAGGCCATAACAATTGTTGAG                   120

TGTTTGAGATAGAGGGAGAATTGAAATATTCTCCCTTTTATCCTTTTTCATTTTAAAC                    180
              -35                                              -10
              agaB
AAATTACGTATAAACATGTATTTAATATATCTTAGGTTGGTCTTTGCTGTGCCCTTTG                    240
              fM  Y  L  I  Y  L  R  L  V  F  C  C  A  L  L                     15

TTGCGGTGTGGCGACAATTCAAAAATTGATAGTGCAACGGATTGCCGGTTGAACAAGAA                   300
L  G  C  G  D  N  S  K  F  D  S  A  T  D  L  P  V  E  Q  E                    35

CAAGAACAGGAAACGGAAACAAGAGGGAGAACCCGAAGAAAGTTCGGAGCAAGACCTGTC                  360
Q  E  Q  E  T  E  Q  E  G  E  P  E  E  S  S  E  Q  D  L  V                    55

GAGGAGGTCGATTGGAAGGATATTCCCGTACCGCCGATGCAGGACCGAATATGAAGTGG                   420
E  E  V  D  W  K  D  I  P  V  P  A  D  A  G  P  N  M  K  W                    75

GAGTTCAAGAGATTTCGGATAATTTGAATATGAGGCCCCTGCGATAATAAGGGGAGT                     480
E  F  Q  E  I  S  D  N  F  E  Y  E  A  P  A  D  N  K  G  S                    95

GAATTCTCGAAAAGTGGACGATTTTATCACAATGCCTGGCCAGGGCCAGGGCTGACC                     540
E  F  L  E  K  W  D  D  F  Y  H  N  A  W  A  G  P  G  L  T                   115

GAATGGAAAACGGGACAGGTCCTATGTAGCCGATGGCGAGCTAAAGATGTGGGCGACAAGA                 600
E  W  K  R  D  R  S  Y  V  A  D  G  E  L  K  M  W  A  T  R                   135

AAACCGGGCTCCGATAAATAAAACATGGGGTGCATTACTTCTAAGACCCGAGTGGTCTAT                  660
K  P  G  S  D  K  I  N  M  G  C  I  T  S  K  T  R  V  V  Y                   155

CCTGTTTATATTGAAGCAAGGGCAAAGGTCATGAACTCATACCTTGGCTTCGGATGTTTGG                720
P  V  Y  I  E  A  R  A  K  V  M  N  S  T  L  A  S  D  V  W                   175
```

```
CTCTTAAGTGCCGATGACACCCAAGAGATAGATATTCTAGAGGCATATGGGCGATTAT         780
 L   L   S   A   D   D   T   Q   E   I   D   I   L   E   A   Y   G   A   D   Y    195
              XbaI           NdeI

TCCGAAAGTGCCGAAAGGATCATTCCTATTTTCTAAAAAGGTACACATAAGCCATCAC         840
 S   E   S   A   G   K   D   H   S   Y   F   S   K   K   V   H   I   S   H   H    215

GTCTTTATTCGAGACCCATTTCAAGATTATCAACCAAAGGATGCCGGTTCTTGGTTCGAA       900
 V   F   I   R   D   P   F   Q   D   Y   Q   P   K   D   A   G   S   W   F   E    235
                                                              NcoI

GACGGCACCGTCTGGAACAAAGAGTTCCATAGGTTTGGTGTGTATTGGAGGGATCCATGG       960
 D   G   T   V   W   N   K   E   F   H   R   F   G   V   Y   W   R   D   P   W    255
     XbaI

CATCTAGAATATTACATAGACGGTGTTCTGGTGAGGACCGTTTCGGGAAAGGACATTATC      1020
 H   L   E   Y   Y   I   D   G   V   L   V   R   T   V   S   G   K   D   I   I    275

GACCCCAAACACTTTACGAATACAACGGATCCCGGTAATACGGAAATGATACCCGCACC      1080
 D   P   K   H   F   T   N   T   T   D   P   G   N   T   E   I   D   T   R   T    295

GGTCTCAATAAAGAAATGGATATTATTAATACCATACGCCAACGGACAATGAATTGAGCAATATA  1140
 G   L   N   K   E   M   D   I   I   N   T   E   D   Q   T   W   R   S   S        315

CCGGCCTCGGGTTACAGTCTAATACTGTGATTGGATCAGGATCTATAAACCTGTAGAGAAATAAGAA 1200
 P   A   S   G   L   Q   S   N   T   Y   T   P   T   D   N   E   L   S   N   I    335

GAAAACAATACGTTCGGGTGTCGATTGGATCGATCAGGATCTATAAACCTGTATCAAATAGTT    1260
 E   N   T   F   G   V   D   W   I   R   I   Y   K   P   V   E   K   Ter          354

AATCCTTCTTTGCTTGGTCGGCGCCCGTGAGCTTGTTCAAACTACTGCCTATGGTTTTTTTATG   1320

TTATAAAACCATAGGTAGTTCCCCCTTTGTTCAAACTACTGCCTATGGTTTTTTTATG        1380
                                              NdeI

TTTTATTCCAGAAAGATGACTGGGGTCATATGATGTTATTTATCTTTTTCTTCCCATAAA      1440
```

FIG.3B
(CONTINUATION)

```
AACATTACCGAAAAGGGCTTGACCTAGCGGTGATTTTAGTTAATTTCATGCTGAGATTT    1500
              -35                            -10
ACGTCTTCGTTAATAAACATCAAGATGGAGTATATAGATTATTACAAGGTTTTGGGCGT    1560
                    fM  E  Y  I  D  Y  Y  K  V  L  G  V
ACCCAAGAATGCCACTGAAAAGGAAATTAAAAAGCATACAGAAAACTGGCAAGAAAGTA    1620
 P  K  N  A  T  E  K  E  I  K  K  A  Y  R  K  L  A  R  K  Y
CCATCCTGATGTAAACCCCAACGATGCGGCTGCCGAGAAAAATTCAAGGCGGCCAAGGA    1680
 H  P  D  V  N  P  N  D  A  A  A  E  K  K  F  K  A  A  K  E
GGCCAACGAGGCCAATGAGGTTTGGGCGATCCTGAAAAGGCGAAAGAAATACGACCAG
 A  N  E  A  N  E  V  L  G  D  P  E  K  R  K  K  Y  D  Q
```

FIG.3B
(CONTINUATION)

```
AgaA    1  MKKNYLLLYFIFLLCGS-------------------------------   17
           ||  |     |
AgaB    1  ---MYLI-YLRLVFCCALLLGCGDNSKFDSATDLPVEQEQEQETEQEGEP  46

AgaA   18  --------IAAQDWNGIPVPANPGNGMTWQLQDNVSDSFNYTSSEGNRPT  59
                   ||  |||||  |   |  |   ||  | |     |
AgaB   47  EESSEQDLVEEVDWKDIPVPADAGPNMKWEFQE-ISDNFEYEAPADNKGS  95

AgaA   60  AFTSKWKPSYINGWTGPGSTIFNAAQAWTNGSQLAIQA-QPAGNGKSYNG  108
            |  ||   |  | ||| |                  |    |    |
AgaB   96  EFLEKWDDFYHNAWAGPGLTEWKRDRSYVADGELKMWATRKPGSDKINMG  145

AgaA  109  IITSKNKIQYPVYMEIKAKIMDQVLANAFWTLTDDETQEIDIMEGYGSD-  157
           ||||    ||||  |  || !   ||. | |  ||||||| | ||  |
AgaB  146  CITSKTRVVYPVYIEARAKVMNSTLASDVWLLSADDTQEIDILEAYGADY  195
                                                    ↑    ↑

AgaA  158  -----RGGTWFAQRMHLSHHTFIRNPFTDYQPMGDATWYYNGGTPWRSAY  202
                | ||| ||| || |||| ||        ||  ||
AgaB  196  SESAGKDHSYFSKKVHISHHVFIRDPFQDYQPK-DAGSWFEDGTVWNKEF  244

AgaA  203  HRYGCYWKDPFTLEYYIDGVKVRTVTRAEIDPNNHLGG-----------  240
           || | || ||  |||||||||  ||||   |   |  |
AgaB  245  HRFGVYWRDPWHLEYYIDGVLVRTVSGKDIIDPKHFTNTTDPGNTEIDTR 294

AgaA  241  TGLNQATNIIIDCENQTDWR--PAA---------TQEELADDSKNIFWVD  279
           ||||   ||| | || || ||               |  |        ||||
AgaB  295  TGLNKEMDIIINTEDQT-WRSSPASGLQSNTYTPTDNELSNIENNTFGVD  343

AgaA  280  WIRVYKPVAVSGGGNNGNDGATEFQYDLGTDTSAVWPGYTRVSNTTRAGN  329
           ||| ||||
AgaB  344  WIRIYKPVEK                                         353
```

FIG.4

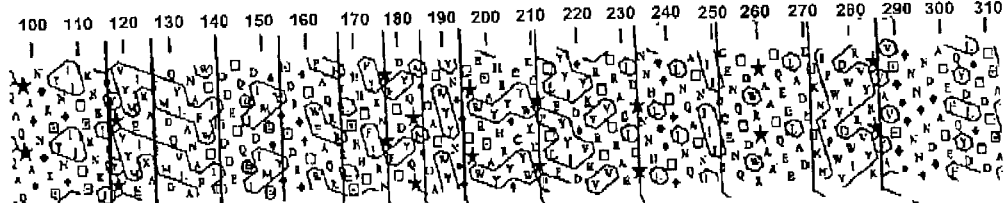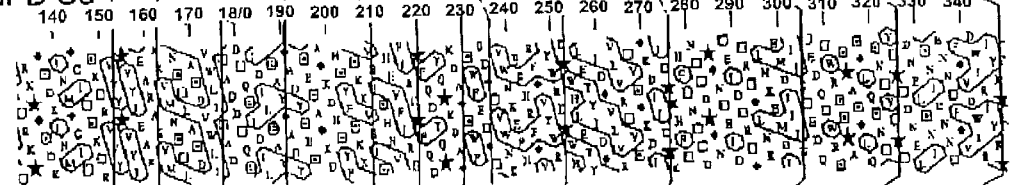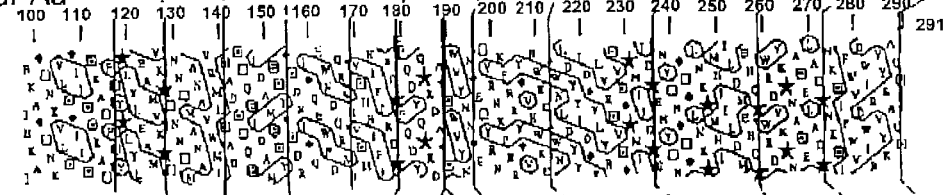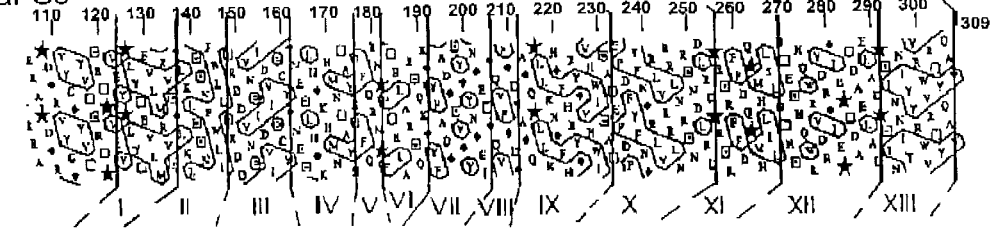
FIG.5

(CONTINUATION)

SEQUENCE LISTING

<160> NUMBER OF SEQ ID NOS: 6

<210> SEQ ID NO 1
<211> LENGTH: 2035
<212> TYPE: DNA
<213> ORGANISM: Cytophaga drobachiensis
<220> FEATURE:
<221> NAME/KEY: CDS
<222> LOCATION: (166)..(1782)

<400> SEQUENCE: 1

```
ttattcttac taatattgta ggaaaattta acacaaaaaa catctttgtt cagttttgt       60 cgagttggta aaacctagaa aacagacacg gcattgtata tttggcgatg attcatctgt     120
ttgtttgttg aatacatttt tattaacccc taaaattaca ttatc atg aaa aaa aat    177
                                               Met Lys Lys Asn
                                                 1 tat ctt tta ctg tat ttt att ttt ctt ttg tgt ggc tct atc gct gca      225
Tyr Leu Leu Leu Tyr Phe Ile Phe Leu Leu Cys Gly Ser Ile Ala Ala
  5              10                  15                  20 cag gac tgg aac gga att cct gta cct gcc aat ccc gga aat ggt atg      273
Gln Asp Trp Asn Gly Ile Pro Val Pro Ala Asn Pro Gly Asn Gly Met
             25                  30                  35 act tgg caa tta cag gat aat gtt tcg gat agt ttt aat tac aca agt      321
Thr Trp Gln Leu Gln Asp Asn Val Ser Asp Ser Phe Asn Tyr Thr Ser
         40                  45                  50 agt gaa gga aat agg cct act gcc ttt act agt aaa tgg aaa cct tcc      369
Ser Glu Gly Asn Arg Pro Thr Ala Phe Thr Ser Lys Trp Lys Pro Ser
     55                  60                  65 tat atc aat gga tgg act ggt cct gga tca aca att ttt aat gcc gcg      417
Tyr Ile Asn Gly Trp Thr Gly Pro Gly Ser Thr Ile Phe Asn Ala Ala
 70                  75                  80 cag gca tgg acc aat ggt tct caa ttg gca att cag gca caa cca gca      465
Gln Ala Trp Thr Asn Gly Ser Gln Leu Ala Ile Gln Ala Gln Pro Ala
 85                  90                  95                 100 ggg aat gga aaa tct tac aac gga att atc acc tcc aaa aat aag atc      513
Gly Asn Gly Lys Ser Tyr Asn Gly Ile Ile Thr Ser Lys Asn Lys Ile
                105                 110                 115 cag tac ccg gtg tat atg gaa att aag gcc aag ata atg gac cag gta      561
Gln Tyr Pro Val Tyr Met Glu Ile Lys Ala Lys Ile Met Asp Gln Val
            120                 125                 130 cta gca aat gct ttc tgg acc ttg act gac gac gag act cag gaa att      609
Leu Ala Asn Ala Phe Trp Thr Leu Thr Asp Asp Glu Thr Gln Glu Ile
        135                 140                 145 gat att atg gaa ggc tat ggc agt gat cgg ggg gga act tgg ttc gcc      657
Asp Ile Met Glu Gly Tyr Gly Ser Asp Arg Gly Gly Thr Trp Phe Ala
    150                 155                 160 caa aga atg cat ttg agc cac cat aca ttt att cgt aac ccc ttt acg      705
Gln Arg Met His Leu Ser His His Thr Phe Ile Arg Asn Pro Phe Thr
165                 170                 175                 180 gat tat cag cct atg gga gac gct aca tgg tat tac aac gga ggt aca      753
Asp Tyr Gln Pro Met Gly Asp Ala Thr Trp Tyr Tyr Asn Gly Gly Thr
                185                 190                 195 cca tgg cgt tca gca tat cac cgt tat gga tgt tat tgg aaa gat cca      801
Pro Trp Arg Ser Ala Tyr His Arg Tyr Gly Cys Tyr Trp Lys Asp Pro
            200                 205                 210 ttt aca ttg gaa tat tat att gac ggg gta aag gtt aga acg gtc aca      849
Phe Thr Leu Glu Tyr Tyr Ile Asp Gly Val Lys Val Arg Thr Val Thr
        215                 220                 225
```

-continued

```
aga gcc gaa att gat cct aat aat cat ctc ggc gga aca ggt ttg aat        897
Arg Ala Glu Ile Asp Pro Asn Asn His Leu Gly Gly Thr Gly Leu Asn
    230                 235                 240 cag gca aca aat att att att gat tgt gaa aat caa aca gat tgg agg        945
Gln Ala Thr Asn Ile Ile Ile Asp Cys Glu Asn Gln Thr Asp Trp Arg
245                 250                 255                 260 ccc gcg gct act caa gaa gaa ctg gcc gat gat agc aaa aat atc ttc        993
Pro Ala Ala Thr Gln Glu Glu Leu Ala Asp Asp Ser Lys Asn Ile Phe
                265                 270                 275 tgg gtc gat tgg ata cgt gtg tac aag cct gtt gcg gta agt gga ggt       1041
Trp Val Asp Trp Ile Arg Val Tyr Lys Pro Val Ala Val Ser Gly Gly
            280                 285                 290 gga aac aac ggt aac gac ggt gcc act gaa ttt caa tat gat tta gga       1089
Gly Asn Asn Gly Asn Asp Gly Ala Thr Glu Phe Gln Tyr Asp Leu Gly
        295                 300                 305 acg gac acc tcg gca gta tgg cca ggg tat aca cgg gtt tcc aac acc       1137
Thr Asp Thr Ser Ala Val Trp Pro Gly Tyr Thr Arg Val Ser Asn Thr
    310                 315                 320 act agg gct ggt aat ttt gga tgg gcg aac acc aat gac atc gga tca       1185
Thr Arg Ala Gly Asn Phe Gly Trp Ala Asn Thr Asn Asp Ile Gly Ser
325                 330                 335                 340 aga gat cgt ggg gct tct aac gga agg aac aat ata aac cgt gat att       1233
Arg Asp Arg Gly Ala Ser Asn Gly Arg Asn Asn Ile Asn Arg Asp Ile
                345                 350                 355 aat ttt agt tca caa act agg ttc ttc act caa gac cta tcc aat ggc       1281
Asn Phe Ser Ser Gln Thr Arg Phe Phe Thr Gln Asp Leu Ser Asn Gly
            360                 365                 370 act tat aac gta ttg atc act ttt ggg gac acc tat gcc cga aaa aat       1329
Thr Tyr Asn Val Leu Ile Thr Phe Gly Asp Thr Tyr Ala Arg Lys Asn
        375                 380                 385 atg aac gtc gcg gcc gaa ggg caa aat aaa tta aca aac ata aac acc       1377
Met Asn Val Ala Ala Glu Gly Gln Asn Lys Leu Thr Asn Ile Asn Thr
    390                 395                 400 aat gcc ggg caa tat gtt agt agg tcg ttt gac gta aat gtc aac gac       1425
Asn Ala Gly Gln Tyr Val Ser Arg Ser Phe Asp Val Asn Val Asn Asp
405                 410                 415                 420 gga aaa cta gat ttg cga ttt tca gtt ggt aat ggc ggg gat gtg tgg       1473
Gly Lys Leu Asp Leu Arg Phe Ser Val Gly Asn Gly Gly Asp Val Trp
                425                 430                 435 tcc att aca aga atc tgg att aga aaa gtt acg agc aac agc gct aat       1521
Ser Ile Thr Arg Ile Trp Ile Arg Lys Val Thr Ser Asn Ser Ala Asn
            440                 445                 450 ttg tta gcg gca aaa gga tta aca ttg gaa gat cct gtg gaa act acg       1569
Leu Leu Ala Ala Lys Gly Leu Thr Leu Glu Asp Pro Val Glu Thr Thr
        455                 460                 465 gaa ttt tta tat cct aac ccc gca aaa aca gat gat ttt gtg act gtt       1617
Glu Phe Leu Tyr Pro Asn Pro Ala Lys Thr Asp Asp Phe Val Thr Val
    470                 475                 480 ccc aat agt gaa att gga agt agt ata atc atc tat aat agt gca ggt       1665
Pro Asn Ser Glu Ile Gly Ser Ser Ile Ile Ile Tyr Asn Ser Ala Gly
485                 490                 495                 500 caa gta gtg aaa aaa gta agt gtg gtt tcc gaa aat cag aaa ata tca       1713
Gln Val Val Lys Lys Val Ser Val Val Ser Glu Asn Gln Lys Ile Ser
                505                 510                 515 cta gaa gga ttt gct aaa gga atg tac ttt atc aat ttg aat ggt cag       1761
Leu Glu Gly Phe Ala Lys Gly Met Tyr Phe Ile Asn Leu Asn Gly Gln
            520                 525                 530 agt aca aaa ctt att gtc caa taaacacaat aacaatttca attaaacgac          1812
Ser Thr Lys Leu Ile Val Gln
                535
```

```
aaaggcgctc tgatgataca gaaaggcctt tgtcgttttt taagttactt caggaaccaa    1872
gataaatttt taggtggtat tgttagcttc ttctaactag aatatgatct gtgttttgcg    1932
ggcttcttgt acttgctgta accgcttcgt ttttgtgcaa tgtcggcaca tggtgtatgc    1992
cctgtttact gggtaaatta ggtacttttc tttttgaagc tta                      2035
```

<210> SEQ ID NO 2
<211> LENGTH: 539
<212> TYPE: PRT
<213> ORGANISM: Cytophaga drobachiensis

<400> SEQUENCE: 2

```
Met Lys Lys Asn Tyr Leu Leu Tyr Phe Ile Phe Leu Leu Cys Gly
  1               5                  10                  15

Ser Ile Ala Ala Gln Asp Trp Asn Gly Ile Pro Val Pro Ala Asn Pro
             20                  25                  30

Gly Asn Gly Met Thr Trp Gln Leu Gln Asp Asn Val Ser Asp Ser Phe
             35                  40                  45

Asn Tyr Thr Ser Ser Glu Gly Asn Arg Pro Thr Ala Phe Thr Ser Lys
     50                  55                  60

Trp Lys Pro Ser Tyr Ile Asn Gly Trp Thr Gly Pro Gly Ser Thr Ile
 65                  70                  75                  80

Phe Asn Ala Ala Gln Ala Trp Thr Asn Gly Ser Gln Leu Ala Ile Gln
                 85                  90                  95

Ala Gln Pro Ala Gly Asn Gly Lys Ser Tyr Asn Gly Ile Ile Thr Ser
            100                 105                 110

Lys Asn Lys Ile Gln Tyr Pro Val Tyr Met Glu Ile Lys Ala Lys Ile
        115                 120                 125

Met Asp Gln Val Leu Ala Asn Ala Phe Trp Thr Leu Thr Asp Asp Glu
    130                 135                 140

Thr Gln Glu Ile Asp Ile Met Glu Gly Tyr Gly Ser Asp Arg Gly Gly
145                 150                 155                 160

Thr Trp Phe Ala Gln Arg Met His Leu Ser His Thr Phe Ile Arg
                165                 170                 175

Asn Pro Phe Thr Asp Tyr Gln Pro Met Gly Asp Ala Thr Trp Tyr Tyr
            180                 185                 190

Asn Gly Gly Thr Pro Trp Arg Ser Ala Tyr His Arg Tyr Gly Cys Tyr
        195                 200                 205

Trp Lys Asp Pro Phe Thr Leu Glu Tyr Tyr Ile Asp Gly Val Lys Val
    210                 215                 220

Arg Thr Val Thr Arg Ala Glu Ile Asp Pro Asn Asn His Leu Gly Gly
225                 230                 235                 240

Thr Gly Leu Asn Gln Ala Thr Asn Ile Ile Asp Cys Glu Asn Gln
                245                 250                 255

Thr Asp Trp Arg Pro Ala Ala Thr Gln Glu Glu Leu Ala Asp Asp Ser
            260                 265                 270

Lys Asn Ile Phe Trp Val Asp Trp Ile Arg Val Tyr Lys Pro Val Ala
        275                 280                 285

Val Ser Gly Gly Asn Asn Gly Asn Asp Gly Ala Thr Glu Phe Gln
    290                 295                 300

Tyr Asp Leu Gly Thr Asp Thr Ser Ala Val Trp Pro Gly Tyr Thr Arg
305                 310                 315                 320

Val Ser Asn Thr Thr Arg Ala Gly Asn Phe Gly Trp Ala Asn Thr Asn
                325                 330                 335
```

-continued

```
Asp Ile Gly Ser Arg Asp Arg Gly Ala Ser Asn Gly Arg Asn Asn Ile
        340                 345                 350

Asn Arg Asp Ile Asn Phe Ser Ser Gln Thr Arg Phe Phe Thr Gln Asp
    355                 360                 365

Leu Ser Asn Gly Thr Tyr Asn Val Leu Ile Thr Phe Gly Asp Thr Tyr
    370                 375                 380

Ala Arg Lys Asn Met Asn Val Ala Ala Glu Gly Gln Asn Lys Leu Thr
385                 390                 395                 400

Asn Ile Asn Thr Asn Ala Gly Gln Tyr Val Ser Arg Ser Phe Asp Val
                405                 410                 415

Asn Val Asn Asp Gly Lys Leu Asp Leu Arg Phe Ser Val Gly Asn Gly
            420                 425                 430

Gly Asp Val Trp Ser Ile Thr Arg Ile Trp Ile Arg Lys Val Thr Ser
        435                 440                 445

Asn Ser Ala Asn Leu Leu Ala Lys Gly Leu Thr Leu Glu Asp Pro
    450                 455                 460

Val Glu Thr Thr Glu Phe Leu Tyr Pro Asn Pro Ala Lys Thr Asp Asp
465                 470                 475                 480

Phe Val Thr Val Pro Asn Ser Glu Ile Gly Ser Ser Ile Ile Tyr
                485                 490                 495

Asn Ser Ala Gly Gln Val Val Lys Lys Val Ser Val Val Ser Glu Asn
            500                 505                 510

Gln Lys Ile Ser Leu Glu Gly Phe Ala Lys Gly Met Tyr Phe Ile Asn
        515                 520                 525

Leu Asn Gly Gln Ser Thr Lys Leu Ile Val Gln
    530                 535

<210> SEQ ID NO 3
<211> LENGTH: 1440
<212> TYPE: DNA
<213> ORGANISM: Cytophaga drobachiensis
<220> FEATURE:
<221> NAME/KEY: CDS
<222> LOCATION: (196)..(1254)

<400> SEQUENCE: 3
gtctttatca caattctatc ttagaattct tactaatgct gacaaaacta cggctgcaac      60
cgtgtattac gataacttct ctatcattga aaaagaagag aggccataac aattgttgag     120
tgtttgagat agagggagaa ttgaaatatt ctccctttttt atccttttttt cattttaaac   180 aaattacgta taaac atg tat tta ata tat ctt agg ttg gtc ttt tgc tgt     231
                 Met Tyr Leu Ile Tyr Leu Arg Leu Val Phe Cys Cys
                   1               5                  10 gcc ctt ttg ttg ggg tgt ggc gac aat tca aaa ttt gat agt gca acg        279
Ala Leu Leu Leu Gly Cys Gly Asp Asn Ser Lys Phe Asp Ser Ala Thr
            15                  20                  25 gat ttg ccg gtt gaa caa gaa caa gaa cag gaa acg gaa caa gag gga        327
Asp Leu Pro Val Glu Gln Glu Gln Glu Gln Glu Thr Glu Gln Glu Gly
        30                  35                  40 gaa ccc gaa gaa agt tcg gag caa gac ctt gtc gag gag gtc gat tgg        375
Glu Pro Glu Glu Ser Ser Glu Gln Asp Leu Val Glu Glu Val Asp Trp
    45                  50                  55                  60 aag gat att ccc gta ccc gcc gat gca gga ccg aat atg aag tgg gag        423
Lys Asp Ile Pro Val Pro Ala Asp Ala Gly Pro Asn Met Lys Trp Glu
                65                  70                  75 ttt caa gag att tcc gat aat ttt gaa tat gag gcc cct gcg gat aat        471
Phe Gln Glu Ile Ser Asp Asn Phe Glu Tyr Glu Ala Pro Ala Asp Asn
```

-continued

```
             80                  85                  90
aag ggg agt gaa ttt ctc gaa aag tgg gac gat ttt tat cac aat gcc    519
Lys Gly Ser Glu Phe Leu Glu Lys Trp Asp Asp Phe Tyr His Asn Ala
         95                 100                 105 tgg gca ggc cca ggg ctg acc gaa tgg aaa cgg gac agg tcc tat gta    567
Trp Ala Gly Pro Gly Leu Thr Glu Trp Lys Arg Asp Arg Ser Tyr Val
    110                 115                 120 gcc gat ggc gag cta aag atg tgg gcg aca aga aaa ccg ggc tcc gat    615
Ala Asp Gly Glu Leu Lys Met Trp Ala Thr Arg Lys Pro Gly Ser Asp
125                 130                 135                 140 aaa ata aac atg ggg tgc att act tct aag acc cga gtg gtc tat cct    663
Lys Ile Asn Met Gly Cys Ile Thr Ser Lys Thr Arg Val Val Tyr Pro
                145                 150                 155 gtt tat att gaa gca agg gca aag gtc atg aac tct acc ttg gct tcg    711
Val Tyr Ile Glu Ala Arg Ala Lys Val Met Asn Ser Thr Leu Ala Ser
            160                 165                 170 gat gtt tgg ctc tta agt gcc gat gac acc caa gag ata gat att cta    759
Asp Val Trp Leu Leu Ser Ala Asp Asp Thr Gln Glu Ile Asp Ile Leu
        175                 180                 185 gag gca tat ggg gcc gat tat tcc gaa agt gcc gga aag gat cat tcc    807
Glu Ala Tyr Gly Ala Asp Tyr Ser Glu Ser Ala Gly Lys Asp His Ser
    190                 195                 200 tat ttt tct aaa aag gta cac ata agc cat cac gtc ttt att cga gac    855
Tyr Phe Ser Lys Lys Val His Ile Ser His His Val Phe Ile Arg Asp
205                 210                 215                 220 cca ttt caa gat tat caa cca aag gat gcc ggt tct tgg ttc gaa gac    903
Pro Phe Gln Asp Tyr Gln Pro Lys Asp Ala Gly Ser Trp Phe Glu Asp
                225                 230                 235 ggc acc gtc tgg aac aaa gag ttc cat agg ttt ggt gtg tat tgg agg    951
Gly Thr Val Trp Asn Lys Glu Phe His Arg Phe Gly Val Tyr Trp Arg
            240                 245                 250 gat cca tgg cat cta gaa tat tac ata gac ggt gtt ctg gtg agg acc    999
Asp Pro Trp His Leu Glu Tyr Tyr Ile Asp Gly Val Leu Val Arg Thr
        255                 260                 265 gtt tcg gga aag gac att atc gac ccc aaa cac ttt acg aat aca acg   1047
Val Ser Gly Lys Asp Ile Ile Asp Pro Lys His Phe Thr Asn Thr Thr
    270                 275                 280 gat ccc ggt aat acg gaa atc gat acc cgc acc ggt ctc aat aaa gaa   1095
Asp Pro Gly Asn Thr Glu Ile Asp Thr Arg Thr Gly Leu Asn Lys Glu
285                 290                 295                 300 atg gat att att atc aat aca gaa gac caa act tgg cgg tct tca ccg   1143
Met Asp Ile Ile Ile Asn Thr Glu Asp Gln Thr Trp Arg Ser Ser Pro
                305                 310                 315 gcc tcg ggt tta cag tct aat acc tat acg cca acg gac aat gaa ttg   1191
Ala Ser Gly Leu Gln Ser Asn Thr Tyr Thr Pro Thr Asp Asn Glu Leu
            320                 325                 330 agc aat ata gaa aac aat acg ttc ggg gtc gat tgg atc agg atc tat   1239
Ser Asn Ile Glu Asn Asn Thr Phe Gly Val Asp Trp Ile Arg Ile Tyr
        335                 340                 345 aaa cct gta gag aaa taagaaaatc cttctttttgc tttggtcgcg cccgtgagct   1294
Lys Pro Val Glu Lys
        350 tatgattcgg cgctgtctaa atagttttat aaaaccatag gtagttcccc ctttgttcaa   1354 actacttgcc tatggttttt tttatgtttt attccagaaa gatgactggg gtcatatgat   1414 gttatttatc ttttcttcc cataaa                                         1440

<210> SEQ ID NO 4
<211> LENGTH: 353
```

```
<212> TYPE: PRT
<213> ORGANISM: Cytophaga drobachiensis

<400> SEQUENCE: 4

Met Tyr Leu Ile Tyr Leu Arg Leu Val Phe Cys Cys Ala Leu Leu Leu
 1               5                  10                  15

Gly Cys Gly Asp Asn Ser Lys Phe Asp Ser Ala Thr Asp Leu Pro Val
            20                  25                  30

Glu Gln Glu Gln Glu Gln Thr Glu Gln Glu Gly Glu Pro Glu Glu
        35                  40                  45

Ser Ser Glu Gln Asp Leu Val Glu Glu Val Asp Trp Lys Asp Ile Pro
     50                  55                  60

Val Pro Ala Asp Ala Gly Pro Asn Met Lys Trp Glu Phe Gln Glu Ile
 65              70                  75                  80

Ser Asp Asn Phe Glu Tyr Glu Ala Pro Ala Asp Asn Lys Gly Ser Glu
                85                  90                  95

Phe Leu Glu Lys Trp Asp Asp Phe Tyr His Asn Ala Trp Ala Gly Pro
            100                 105                 110

Gly Leu Thr Glu Trp Lys Arg Asp Arg Ser Tyr Val Ala Asp Gly Glu
        115                 120                 125

Leu Lys Met Trp Ala Thr Arg Lys Pro Gly Ser Asp Lys Ile Asn Met
130                 135                 140

Gly Cys Ile Thr Ser Lys Thr Arg Val Val Tyr Pro Val Tyr Ile Glu
145                 150                 155                 160

Ala Arg Ala Lys Val Met Asn Ser Thr Leu Ala Ser Asp Val Trp Leu
                165                 170                 175

Leu Ser Ala Asp Asp Thr Gln Glu Ile Asp Ile Leu Glu Ala Tyr Gly
            180                 185                 190

Ala Asp Tyr Ser Glu Ser Ala Gly Lys Asp His Ser Tyr Phe Ser Lys
        195                 200                 205

Lys Val His Ile Ser His His Val Phe Ile Arg Asp Pro Phe Gln Asp
    210                 215                 220

Tyr Gln Pro Lys Asp Ala Gly Ser Trp Phe Glu Asp Gly Thr Val Trp
225                 230                 235                 240

Asn Lys Glu Phe His Arg Phe Gly Val Tyr Trp Arg Asp Pro Trp His
                245                 250                 255

Leu Glu Tyr Tyr Ile Asp Gly Val Leu Val Arg Thr Val Ser Gly Lys
            260                 265                 270

Asp Ile Ile Asp Pro Lys His Phe Thr Asn Thr Thr Asp Pro Gly Asn
        275                 280                 285

Thr Glu Ile Asp Thr Arg Thr Gly Leu Asn Lys Glu Met Asp Ile Ile
    290                 295                 300

Ile Asn Thr Glu Asp Gln Thr Trp Arg Ser Ser Pro Ala Ser Gly Leu
305                 310                 315                 320

Gln Ser Asn Thr Tyr Thr Pro Thr Asp Asn Glu Leu Ser Asn Ile Glu
                325                 330                 335

Asn Asn Thr Phe Gly Val Asp Trp Ile Arg Ile Tyr Lys Pro Val Glu
            340                 345                 350

Lys

<210> SEQ ID NO 5
<211> LENGTH: 828
<212> TYPE: DNA
<213> ORGANISM: Cytophaga drobachiensis
```

```
<400> SEQUENCE: 5
gcacaggact ggaacggaat tcctgtacct gccaatcccg gaaatggtat gacttggcaa      60
ttacaggata atgtttcgga tagttttaat tacacaagta gtgaaggaaa taggcctact     120
gcctttacta gtaaatggaa accttcctat atcaatggat ggactggtcc tggatcaaca     180
atttttaatg ccgcgcaggc atggaccaat ggttctcaat tggcaattca ggcacaacca     240
gcagggaatg gaaaatctta acggaatt atcacctcca aaataagat ccagtacccg        300 gtgtatatgg aaattaaggc caagataatg gaccaggtac tagcaaatgc tttctggacc     360
ttgactgacg acgagactca ggaaattgat attatggaag ctatggcag tgatcggggg      420 ggaacttggt tcgcccaaag aatgcatttg agccaccata catttattcg taacccctt     480 acggattatc agcctatggg agacgctaca tggtattaca acggaggtac accatggcgt     540
tcagcatatc accgttatgg atgttattgg aaagatccat ttacattgga atattatatt     600 gacgggtaa aggttagaac ggtcacaaga gccgaaattg atcctaataa tcatctcggc      660
ggaacagggt tgaatcaggc aacaaatatt attattgatt gtgaaaatca aacagattgg     720
aggcccgcgg ctactcaaga gaactggcc gatgatagca aaaatatctt ctgggtcgat      780
tggatacgtg tgtacaagcc tgttgcggta agtggaggtg gaaacaac                  828

<210> SEQ ID NO 6
<211> LENGTH: 276
<212> TYPE: PRT
<213> ORGANISM: Cytophaga drobachiensis

<400> SEQUENCE: 6

Ala Gln Asp Trp Asn Gly Ile Pro Val Pro Ala Asn Pro Gly Asn Gly
  1               5                  10                  15

Met Thr Trp Gln Leu Gln Asp Asn Val Ser Asp Ser Phe Asn Tyr Thr
             20                  25                  30

Ser Ser Glu Gly Asn Arg Pro Thr Ala Phe Thr Ser Lys Trp Lys Pro
         35                  40                  45

Ser Tyr Ile Asn Gly Trp Thr Gly Pro Gly Ser Thr Ile Phe Asn Ala
     50                  55                  60

Ala Gln Ala Trp Thr Asn Gly Ser Gln Leu Ala Ile Gln Ala Gln Pro
 65                  70                  75                  80

Ala Gly Asn Gly Lys Ser Tyr Asn Gly Ile Ile Thr Ser Lys Asn Lys
                 85                  90                  95

Ile Gln Tyr Pro Val Tyr Met Glu Ile Lys Ala Lys Ile Met Asp Gln
            100                 105                 110

Val Leu Ala Asn Ala Phe Trp Thr Leu Thr Asp Glu Thr Gln Glu
        115                 120                 125

Ile Asp Ile Met Glu Gly Tyr Gly Ser Asp Arg Gly Gly Thr Trp Phe
    130                 135                 140

Ala Gln Arg Met His Leu Ser His His Thr Phe Ile Arg Asn Pro Phe
145                 150                 155                 160

Thr Asp Tyr Gln Pro Met Gly Asp Ala Thr Trp Tyr Tyr Asn Gly Gly
                165                 170                 175

Thr Pro Trp Arg Ser Ala Tyr His Arg Tyr Gly Cys Tyr Trp Lys Asp
            180                 185                 190

Pro Phe Thr Leu Glu Tyr Tyr Ile Asp Gly Val Lys Val Arg Thr Val
        195                 200                 205

Thr Arg Ala Glu Ile Asp Pro Asn Asn His Leu Gly Gly Thr Gly Leu
    210                 215                 220
```

```
Asn Gln Ala Thr Asn Ile Ile Ile Asp Cys Glu Asn Gln Thr Asp Trp
225                 230                 235                 240

Arg Pro Ala Ala Thr Gln Glu Glu Leu Ala Asp Asp Ser Lys Asn Ile
                245                 250                 255

Phe Trp Val Asp Trp Ile Arg Val Tyr Lys Pro Val Ala Val Ser Gly
            260                 265                 270

Gly Gly Asn Asn
        275
```

GENES CODING FOR β-AGARASES AND THEIR USE FOR PRODUCING AGAR BIODEGRADATION ENZYMES

The present invention relates to two novel genes coding for β-agarases and to their use for producing agar biodegradation enzymes.

It further relates to the *Cytophaga drobachiensis* strain from which these genes were isolated.

The sulfated galactans of Rhodophyceae, such as agars and carrageenans, represent the major polysaccharides of Rhodophyceae and are very widely used as gelling agents or thickeners in various branches of activity, especially the agri-foodstuffs sector. Approximately 6000 tonnes of agars and 22,000 tonnes of carrageenans are extracted annually from marine red algae for this purpose. Agars are produced industrially from red algae of the genera Gelidium and Gracilaria. Carrageenans are widely extracted from the genera Chondrus, Gigartina and Euchema.

Agaro-colloids are polysaccharide complexes consisting mainly of agars and agaroids. Each agaro-colloid has a different content of each of the above compounds, so its gelling strength is different. Agar gel comprises a matrix of double-helix polymer chains held together by hydrogen bonds.

There are two types of enzyme capable of degrading agars: α-agarases and β-agarases. β-Agarases act on the β-1,4 linkage and α-agarases act on the α-1,3 linkage.

Microorganisms which produce enzymes capable of hydrolyzing agars have already been isolated. This capacity to digest agar has been attributed to the genera Pseudomonas (MORRICE et al., Eur. J. Biochem. 137, 149–154, (1983)), Streptomyces (HODGSON and CHATER, J. Gen. Microbiol. 124, 339–348, (1981)), Cytophaga (VAN DER MEULEN and HARDER, J. Microbiol. 41, 431–447, (1975)) and Vibrio (SUGANO et al., Appl. Environ. Microbiol. 59, 1549–1554, (1993)). Several β-agarase genes have already been isolated. Thus BELAS et al. isolated the gene of an agarase from *Pseudomonas atlantica* (Appl. Environ. Microbiol. 54, 30–37, (1988)). BUTTNER et al. isolated an agarase from *Streptomyces coelicolor* and sequenced the corresponding gene (Mol. Gen. Genet. 209, 101–109, (1987)). SUGANO et al. cloned and sequenced two different agarase genes from Vibrio sp. JT0107, which they called agaA (Appl. Environ. Microbiol. 59, 3750–3756, (1993)) and agaB (Biochimica et Biophysica Acta 1 218, 105–108, (1994)).

The Applicant has now isolated, from the red alga *Delesseria sanguinea,* a bacterial strain which has agarase activity.

This strain was deposited in the DSMZ Collection (Deutsche Sammlung von Mikroorganismen und Zellkulturen GmbH (German Collection of Microorganisms and Cell Cultures)) on May 8, 1998 under the number DSM 12170. It forms the first subject of the present invention.

Taxonomic investigation of this strain, performed by techniques well known to those skilled in the art, shows that it belongs to the genus Cytophaga (bacteria of the CFB or "Cytophaga/Flexibacter/Bacteroides" group). In fact, this strain develops by spreading and has yellow colonies encrusted in the agar, which is then liquefied. The bacterium is a Gram-negative bacterium and has the shape of a non-mobile rod of 0.3–0.4×3.0–8.0 μm×μm. When a drop of culture of the strain is inoculated at the center of an agar dish, the colony develops with concentric growth of the margin and this mobility is not inhibited by diethyl ether, which is an inhibitor of the flagellar apparatus. The strain is aerobic and has an oxidative metabolism. It produces flexirubin, which is a pigment rarely found in isolates of marine Cytophaga but present in non-marine Cytophaga. It is capable of assimilating various carbon sources and degrading several types of macromolecule such as agar, carrageenan, starch and gelatin.

The Applicant carried out an in-depth study to find out what species this strain belonged to. Thus it determined the percentage guanine and cytosine composition of the DNA of the strain of the invention and found that the values were between 43 and 49%. It also sequenced its 16S DNA by the method well known to those skilled in the art for finding out the taxonomic position of a strain (FOX et al., Int. J. Syst. Bacteriol. 22, 44–57, (1977)). The sequencing result shows that the strain of the invention is very similar to *Cytophaga uliginosa.* (There is a 99% similarity of sequence between the 16S DNA of *C. uliginosa* and that of the strain of the invention.) However, DNA/DNA hybridization between the two strains (45%) shows that they are different species.

Furthermore, the strain of the invention has similar morphological, biochemical and physiological characteristics to the strain *Pseudomonas drobachiensis* nov. comb. isolated by HUMM (Duke Univ. Mar. Stn. Bull. 3, 43–75, (1946)). It was therefore named *Cytophaga drobachiensis.*

The Applicant also isolated two genes with β-agarase activity from *Cytophaga drobachiensis* DSM 12170.

Thus the present invention further relates to the novel agaA gene coding for a β-agarase, which has the DNA sequence SEQ ID No. 1.

It further relates to the novel agaB gene coding for a β-agarase, which has the DNA sequence SEQ ID No. 3.

These two genes code for two different β-agarases produced by *C. drobachiensis* DSM 12170, namely the β-agarases called proteins AgaA and AgaB.

The present invention further relates to the nucleic acid sequences, namely the genomic DNA sequences and the DNA or mRNA sequences, which comprise or consist of a concatenation of nucleotides coding for the protein AgaA or the protein AgaB or for any one of their peptide fragments as defined below.

The invention therefore relates to:

All the nucleic acid sequences coding for the protein AgaA in its entirety or for one or more of its peptide fragments. These sequences are preferably represented by:
  a) the DNA sequence SEQ ID No. 1 coding for the protein AgaA, and its fragments coding for the peptide fragments of said protein;
  b) the DNA sequences which hybridize under specific stringency conditions with the above sequence or one of its fragments;
  c) the DNA sequences which, because of the degeneracy of the genetic code, are derived from one of the sequences a) and b) above and code for the protein AgaA or the fragments of said protein; and
  d) the corresponding mRNA sequences.

All the nucleic acid sequences coding for the protein AgaB in its entirety or for one or more of its peptide fragments. These sequences are preferably represented by:
  a) the DNA sequence SEQ ID No. 3 coding for the protein AgaB, and its fragments coding for the peptide fragments of said protein;
  b) the DNA sequences which hybridize under specific stringency conditions with the above sequence or one of its fragments;
  c) the DNA sequences which, because of the degeneracy of the genetic code, are derived from one of the sequences a) and b) above and code for the protein AgaB or the fragments of said protein; and d) the corresponding mRNA sequences.

The present invention further relates to the nucleic acid sequence SEQ ID No. 5 coding for the specific peptide fragment AgaA', which will be described below. This sequence corresponds to nucleic acids 223–1050 of SEQ ID No. 1.

The invention therefore further relates to the nucleic acid sequences coding for said peptide fragment AgaA' and its peptide fragments, which are represented by:

a) the DNA sequence SEQ ID No. 5 coding for the peptide fragment AgaA', and its fragments coding for the peptide fragments of said peptide fragment AgaA';

b) the DNA sequences which hybridize under specific stringency conditions with the above sequence or one of its fragments;

c) the DNA sequences which, because of the degeneracy of the genetic code, are derived from one of the sequences a) and b) above and code for the peptide fragment AgaA' or the fragments of said fragment; and d) the corresponding mRNA sequences.

The nucleic acids according to the invention can be prepared by chemical synthesis or genetic engineering using the techniques well known to those skilled in the art and described for example in SAMBROOK et al. ("Molecular Cloning: a Laboratory Manual", published by Cold Spring Harbor Press, N.Y., 1989).

For example, the DNA sequences according to the invention can be synthesized by amplifying the genes of *Cytophaga drobachiensis* by the PCR (polymerase chain reaction) method, as described for example by GOBLET et al. (Nucleic Acid Research 17, 2144, (1989)), using, as primers, synthetic oligonucleotides defined from the DNA sequence SEQ ID No. 1 or SEQ ID No. 3.

The nucleic acid fragment amplified in this way can then be cloned into an expression vector by the techniques described in MANIATIS et al. (Molecular Cloning. A laboratory manual, New York (1982)).

The invention further relates to the prokaryotic cells and eukaryotic cells transformed with the aid of an expression vector containing a nucleic acid sequence according to the invention. This expression vector, which can be e.g. in the form of a plasmid, must contain, in addition to the nucleic acid sequence of the invention, the means necessary for its expression, such as, in particular, a promoter, a transcription terminator, an origin of replication and, preferably, a selection marker. The transformation of prokaryotic cells and eukaryotic cells is a technique well known to those skilled in the art, who will easily be able to determine, as a function of the microorganism to be transformed, the means necessary for expression of the DNA sequence according to the invention.

The preferred prokaryotic microorganisms for the purposes of the invention are *Escherichia coli* and *Bacillus subtilis*.

The cells of *Aspergillus niger, Trichoderma viridae* or *Pichia pastoris* may be mentioned in particular as examples of eukaryotic cells which are suitable for the purposes of the invention.

The present invention further relates to the novel protein AgaA of *C. drobachiensis*, which comprises SEQ ID No. 2.

It further relates to the novel protein AgaB of *C. drobachiensis*, which comprises SEQ ID No. 4.

The novel protein AgaA is composed of 539 amino acids and has a theoretical molecular weight of 60.001 kDa. After removal of the signal peptide, this protein has a calculated molecular weight of 57.768 kDa.

The novel protein AgaB is composed of 353 amino acids. After removal of the signal peptide, this protein has a calculated molecular weight of 40.680 kDa.

The present invention further relates to the peptide fragments of the proteins AgaA and AgaB which result from the addition, suppression and/or replacement of one or more amino acids, said peptide fragments having conserved the β-agarase activity.

The present invention further relates to the peptide fragment AgaA', which has SEQ ID No. 6.

This peptide fragment AgaA', composed of 276 amino acids, corresponds to amino acids 20–295 of the protein AgaA.

The invention further relates to the peptide fragments of AgaA' which result from the addition, suppression and/or replacement of one or more amino acids, said peptide fragments having conserved the β-agarase activity.

The proteins and peptide fragments according to the invention can be obtained by the techniques of genetic engineering comprising the following steps:

culture of prokaryotic cells or eukaryotic cells transformed by an expression vector possessing a nucleic acid sequence according to the invention; and recovery of the protein or peptide fragment produced by said cells.

These techniques are well known to those skilled in the art and further details may be obtained by reference to the following work: Recombinant DNA Technology I, editors: Ales Prokop, Raskesh K. Bajpai; Annals of the New York Academy of Sciences, volume 646, 1991.

The peptide fragments can also be prepared by conventional chemical peptide synthesis well known to those skilled in the art.

The invention will now be described in detail with the aid of the experimental section below.

The techniques described in these Examples, which are well known to those skilled in the art, are largely explained in detail in the work by SAMBROOK et al. (supra) or in the work by MANIATIS et al. (supra).

The following description will be understood more clearly with the help of FIGS. 1 to 6, in which:

FIGS. 2A and 2B show the physical maps of the genomic clones of *Cytophaga drobachiensis* which have agarase activity;

FIGS. 3A and 3B give the nucleotide and amino acid sequences deduced from the genes of agarase A (SEQ ID NO: 1) (FIG. 3A) and agarase B (SEQ ID NO: 3) (FIG. 3B) originating from *C. drobachiensis;*

Figure 5:
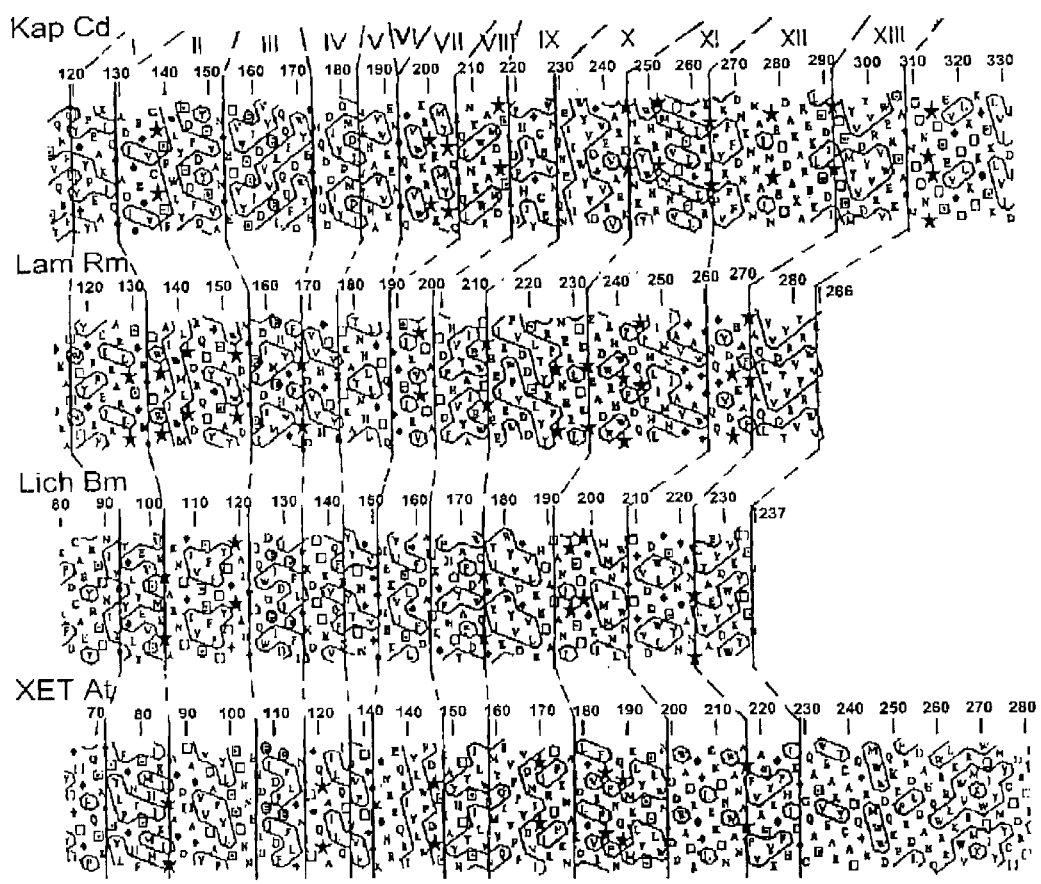
Figure 6A:
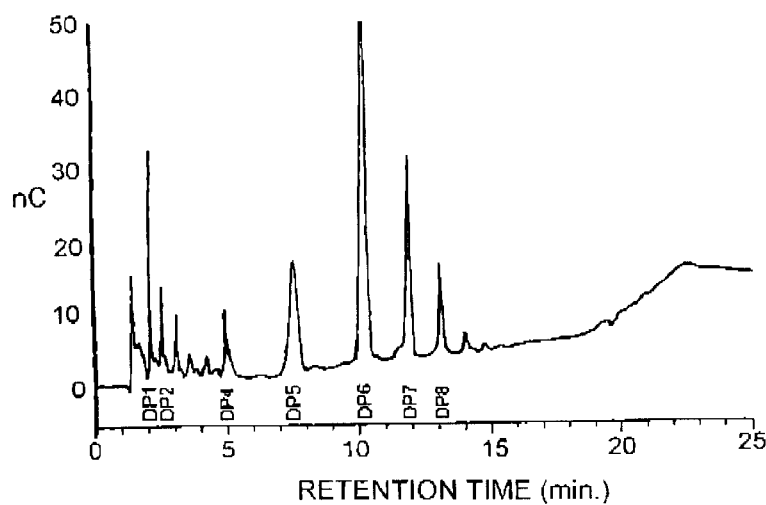
Figure 6B:
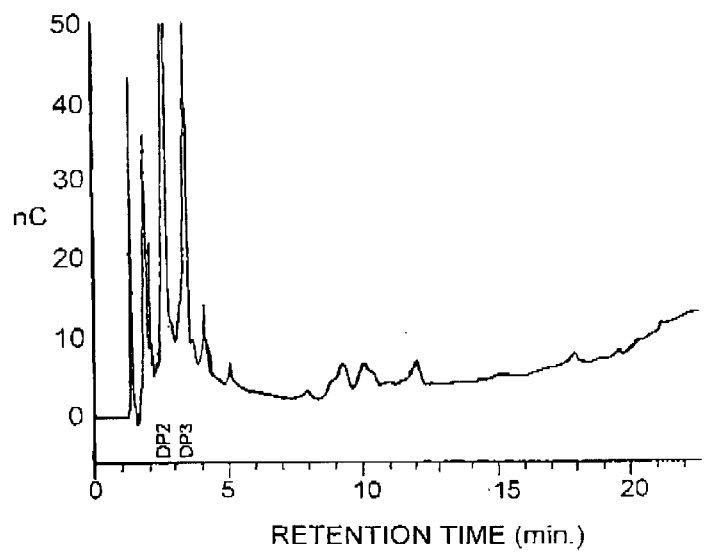
Figure 6C:
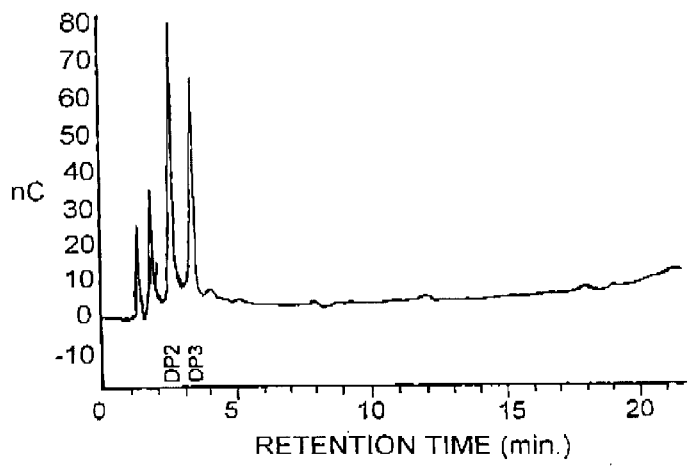

FIG. 4 shows the alignment of the protein AgaA (top line) (SEQ ID NO: 2) and the protein AgaB (bottom line) (SEQ ID NO: 4) originating from the *C. drobachiensis* strain according to the invention;

FIG. 5 shows the hydrophobic cluster analysis (HCA) of the agarase genes and other genes of glycoside hydrolases; and FIGS. 6A to 6C show the elution profiles of the products resulting from the hydrolysis of neoagarododecaose by the agarases originating from the *C. drobachiensis* strain according to the invention.

EXAMPLE 1

Isolation, Culture of the Strain *Cytophaga drobachiensis* DSM 12170 and Extraction of its DNA The strain DSM 12170 was isolated from living fronds of the red alga *Delesseria sanguinea,* the isolation being effected on a Petri dish on Zobell's medium (ZOBELL, J. Mar. Res. 4, 41–75, (1941)) containing 2% of i-carrageenan.

The strain was cultured at 25° C. on Zobell's medium (ZOBELL, J. Mar. Res. 4, 41–75, (1941)).

The protocol employed to extract the DNA from the strain *Cytophaga drobachiensis* DSM 12170 is derived from that of Marmur (MARMUR, J. Mol. Biol. 3, 208–218, (1961)) and is described in detail below.

After culture, the bacteria were centrifuged at 3000 g for 15 min and then washed in sterile seawater. The cells were subjected to a final centrifugation, identical to the previous one, and were treated immediately or frozen at −20° C.

5 to 10 g of cells, depending on the cell concentration (moist weight after centrifugation), were taken up in 25 ml of Sph buffer (50 mM Tris-HCl, pH 8; 25% sucrose) and then in 5 ml of TES buffer (50 mM Tris-HCl, pH 8; 5 mM ethylenediaminetetraacetic acid; 50 mM sodium chloride) and 50 mg of lysozyme were added. Spheroplasts appeared after incubation for 15 min at room temperature.

The DNA was immediately protected by adding 100 mM ethylenediaminetetraacetic acid (final concentration), and incubation was continued in ice for a further 10 min.

Lysis was brought to completion by adding 2% of sodium dodecylsulfate (final concentration) and 25 ml of lysis solution (50 mM Tris-HCl, pH 8; 100 mM ethylenediaminetetraacetic acid; 100 mM sodium chloride).

The proteins were fully denatured by incubation for 1 hour at 50° C. in the presence of 40 mg of proteinase K. When this incubation was complete, 1 M sodium perchlorate (final concentration) was added to break the DNA/protein bonds.

The solution was deproteinized by being shaken in the presence of 0.5 volume of saturated phenol for 5 min. The shaking was carried out by hand and had to be sufficiently vigorous to form an emulsion (without which no extraction could take place) but not so vigorous as to tear the DNA. The deproteinization was continued for a further 5 min after adding 0.5 volume of chloroform/isoamyl alcohol (24/1). The proteins were concentrated at the interface between the aqueous phase and the organic phase by centrifugation at 10,000 g for 15 min at room temperature.

The aqueous phase containing the nucleic acids was transferred to a clean tube using a pipette whose tip had been enlarged so as not to tear the DNA. The deproteinization was continued and the traces of phenol were extracted from the aqueous phase by shaking the solution for 5 min in the presence of 1 volume of chloroform/isoamyl alcohol (24/1).

After centrifugation at 10,000 g for 5 min at room temperature, the aqueous phase was withdrawn with the same precautions as above, and the nucleic acids were precipitated by gently pouring in 0.6 volume of isopropanol (to form two phases). The high-molecular DNA was recovered with a glass rod, washed in 70% ethanol, dehydrated in absolute ethanol and dried in air.

After drying, the DNA was dissolved in 20 ml of TE buffer (10 mM Tris-HCl, pH 8; 1 mM ethylenediaminetetraacetic acid). This took about 12 hours and could be facilitated by heating to 50° C. When the solution obtained was opalescent—a sign of substantial contamination with proteins—the latter were efficiently removed by passing a fraction of the DNA over a cesium chloride gradient in the presence of ethidium bromide. After this passage over the gradient and removal of the ethidium bromide, the resulting DNA was quantified. It could be stored at 4° C. or frozen at −20° C.

The DNA composition, expressed as the molar percentage of guanine+cytosine (mol % of G+C), was determined by ULITZUR's spectroscopic method (Biochem. Biophys. Acta 272, 1–11, (1972)) and the cesium chloride gradient method in the presence of 2'-[4-hydroxyphenyl]-5-[4-methylpiperazin-1-yl]-2,5'-bi-1H-benzimidazole (Hoechst 33258/Sigma) (KARLOVSKY and DE COCK, Anal. Biochem. 194, 192–197, (1991)). In the first case it is 44±1% (mean of 2 manipulations) and in the second case it is 48.8%. This molar percentage of G+C was calculated using the DNA of *E. coli* as the standard reference.

EXAMPLE 2

Sequencing of the 16S DNA of *Cytophaga drobachiensis*

The 16S DNA was amplified by PCR using the genomic DNA of the *C. drobachiensis* strain as the template and Taq polymerase (Promega) as the enzyme. The typical PCR reaction mixture, with a volume of 50 μl, had the following composition: 100 ng of template, 10 ng of each of the two oligonucleotides specific for the 16S DNA of the Bacteria kingdom, 200 mM of each of the dNTPs (dNTP being deoxyribonucleoside triphosphate), 1.5 mM $MgCl_2$, Taq buffer and 2.5 U of enzyme. The different PCR steps were as follows:

6 min at 95° C. (once),
1.5 min at 95° C.; 1.5 min at 54° C.; 2.5 min at 72° C. (25 times),
8.5 min at 72° C. (polymerization step).

The product obtained by PCR was either cloned first and then sequenced, or sequenced directly by PCR using Thermosequenase (Amersham) as the enzyme, with different oligonucleotides specific for the 16S DNA, labeled at the 5' end with Texas red. The different PCR steps were as follows:

5 min at 97° C. (once),
1 min at 97° C.; 1 min at 54° C.; 1 min at 61° C. (25 times).

This sequencing, which reveals the taxonomic position of the strain, showed that the strain according to the invention was phylogenetically very close to *Cytophaga uliginosa*.

EXAMPLE 3

Demonstration and Purification of the Agarase Activities in the Strain *Cytophaga drobachiensis* DSM 12170

The agarase activity of the strain was induced in a Zobell medium supplemented with 2.5 mg/l of agar. A strain is considered to exhibit agarase activity when it digests the agar on which it develops.

The strains with agarase activity were cultured in the above medium at 20° C. The culture was centrifuged at 1000 g for 20 min. The culture supernatant was recovered and concentrated to 50 ml by tangential ultrafiltration (cut-off threshold: 10 kDa), this operation being followed by precipitation with ammonium sulfate. The protein residue was resuspended in 9 ml of MES buffer (MES being 2-[N-morpholino]ethanesulfonic acid). 2 ml of Sepharose CL6B were then added for carrying out affinity chromatography. Two fractions were recovered, one of which bound to the Sepharose column.

The agarase activity was tested by assaying the reducing sugars according to the technique of KIDBY D. K. & DAVIDSON D. J. (Annal. Biochem. vol. 55, 321–325, (1973)) in the supernatant before affinity chromatography (which is quite obviously positive) and in the two fractions obtained after chromatography. Agarase activity was detected in each fraction.

Figure 1:
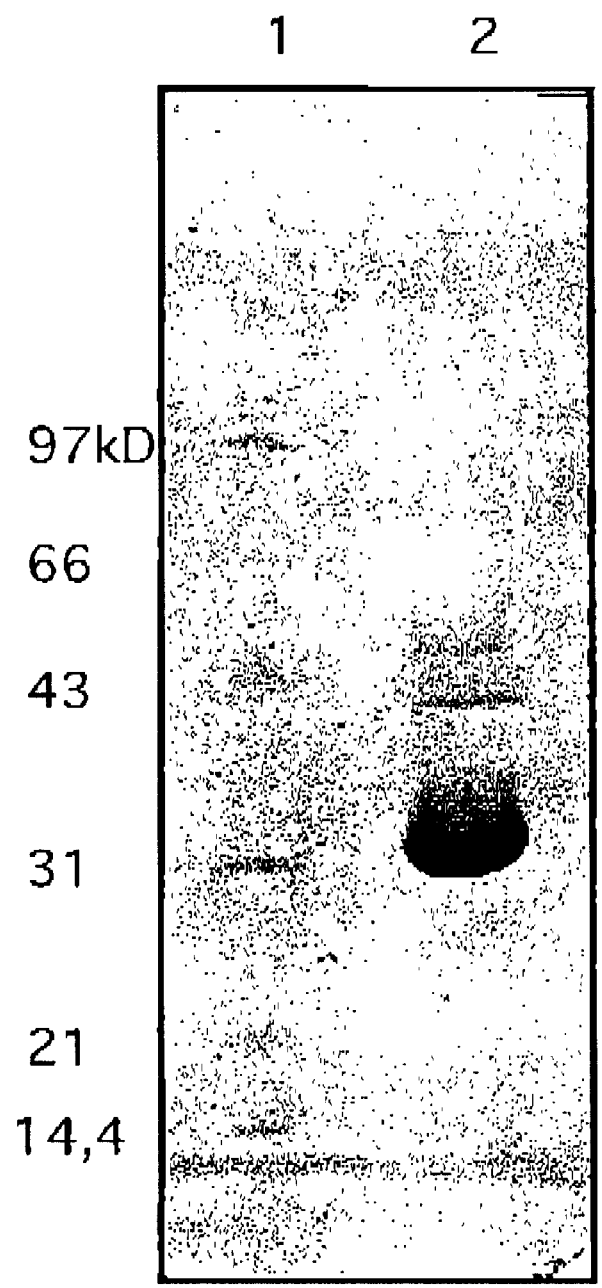
FIG. 1 is a photograph of an SDS-PAGE electrophoresis gel of the culture supernatant of *C. drobachiensis* of the invention.

SDS-PAGE electrophoresis was carried out on the fraction bound to the column. This gave a main band with a mean molecular weight of 31 kDa (FIG. 1). This protein was microsequenced. The sequence of the internal peptide obtained was found in the amino acid sequence deduced from the agaA gene (FIG. 3A).

EXAMPLE 4

Cloning of the Agarase Genes

A genomic DNA library of the *C. drobachiensis* strain was constructed. 4 to 10 kb fragments originating from partial digestion of the chromosomal DNA by NdeII were fractionated on a sucrose gradient. These fragments were inserted into the BamHI site of plasmid pAT153 (TWIGG and SHERRATT, Nature 283, 216, (1980)).

The recombinant clones (about 6000) of the strain *E. coli* DH5α (SAMBROOK et al., supra) were independently inoculated onto microtiter plates in LBA medium (Luria-Bertani medium (MANIATIS et al., supra) supplemented with ampicillin at a concentration of 50 µg/ml). After incubation overnight at 37° C., these clones were plated at 22° C. on Zd medium (5 mg/l of bactotryptone, 1 mg/l of yeast extract, 10 mg/l of NaCl, pH 7.2) supplemented with 50 µg/ml of ampicillin in order to observe the agarase production (hole in the gelose when there is agarase production).

In two months of culture at 22° C., 4 independent colonies, called pAC1 to pAC4, made a hole in the substrate.

The maps of the plasmids corresponding to these colonies are shown in FIGS. 2A and 2B, in which:

the thin lines represent the pAT153 regions, the emboldened segments represent the *C. drobachiensis* inserts and the white rectangles represent the agarase genes; and the various abbreviations have the following meanings:
B/S: BamHI-Sau3A cloning site
B: BamHI
Bg: BglII
C: ClaI
E: EcoRI
H: HindIII
K: KnpI
Nc: NcoI
Nd: NdeI
Ps: PstI
Pv: PvuII
Sa: SalI
Sp: SphI
X: XbaI The mapping of these plasmids therefore shows the presence of two different common fragments, suggesting the presence of at least two agarase genes in the genome of *C. drobachiensis*. Plasmids pAC1 and pAC2 share a common SalI-PstI fragment of 5 kb (delimited by the broken lines in FIG. 2A) and plasmids pAC3 and pAC4 share a common ClaI-PstI fragment of 5 kb (delimited by the broken lines in FIG. 2B).

The two fragments were subcloned into phagemid pBluescript (Stratagène) and are called pASP5 and pACP5, as indicated in FIGS. 2A and 2B. These two subclones have an agarase+phenotype.

EXAMPLE 5

Analysis of the Nucleotide Sequence of the Agarase Genes

Plasmids pASP5 and pACP5 were used to determine, on both strands, the nucleotide sequences of the agarase structural genes.

This sequencing was effected by a technique well known to those skilled in the art, namely Sanger's method (SANGER et al., Proc. Natl. Acad. Sci. 74, 5463–5467, (1977)), which is also called the dideoxynucleotide method.

The pASP5 insert was sequenced over 2980 bp from the BamHI site to the HindIII site (delimited by the letters B/S and H in FIG. 2A). It contains a single open reading frame (ORF) of 1617 bp, called the agaA gene. This gene has SEQ ID No. 1.

The nucleic acid sequence obtained is illustrated in FIG. 3A. Two hexamers, TaGAaA and TATAtT, compatible with the "−35" and "−10" consensus promoters of *E. coli*—the capital letters corresponding to the consensus promoter of *E. coli* (ROSENBERG, M. & COURT, D., Ann. Rev. 13, 319–353, (1979))—and separated by 15 nucleotides, are found 62 nucleotides upstream from the putative start codon of the agaA gene. In the untranslated 3' region, a transcription termination loop is found downstream from the TAA stop codon, followed by three thymidine residues.

The pACP5 insert was sequenced over 2440 bp between the two EcoRI sites (delimited by the two letters E in FIG. 2B). It contains a single complete ORF of 1059 bp, called 2B). It contains a single complete ORF of 1059 bp, called the agaB gene, and a partial ORF. This agaB gene has SEQ ID No. 3.

The nucleic acid sequence obtained is illustrated in FIG. 3B. Two hexamers, TTGAgA and TATtcT, compatible with the "−35" and "−10" consensus promoters of *E. coli* and separated by 17 nucleotides, are found 43 nucleotides upstream from the putative start codon of the agaB gene. In the untranslated 3' region, a transcription termination loop is found downstream from the TAA stop codon, followed by four thymidine residues. The second, partial ORF is found downstream from the agaB gene. Two hexamers, TTGACc and TtaAtT, separated by 17 nucleotides, are also found 39 nucleotides upstream from the putative start codon of the second ORF.

The Chargaff coefficient (GC%) of each of the agarase A and B genes is between 41 and 45%, which is in agreement with that of the genus Cytophaga found by REICHENBACH et al. (30–45%; Genus Cytophaga, in Bergey's Manual of systematic bacteriology, 2015–2050, (1989)).

EXAMPLE 6

Analysis of the Amino Acid Sequence Deduced from the Agarase Genes

The translation product of the agaA gene is a protein of 539 amino acids with a theoretical molecular weight of 60.001 kDa. The deduced amino acid sequence, SEQ ID No. 2, comprises the internal peptide determined from the microsequencing of the purified agarase A (underlined in FIG. 3A). As indicated by analysis of the hydropathy profile (KYTE and DOOLITLE, J. Mol. Biol. 157, 105–132, (1982)), the N-terminal part of the protein corresponds to a very hydrophobic domain, suggesting that this domain is the signal peptide (VON HEIJNE, Eur. J. Biochem. 133, 17–21, (1983); J. Mol. Biol. 184, 99–105, (1985)). According to Von Heijne's "(−3,−1)" rule, the most probable cleavage site of the signal peptidase is assigned between Ala19 and Ala20.

It should be noted that the molecular weight of the protein AgaA calculated after removal of the signal peptide, i.e. about 57.768 kDa, is greater than the molecular weight initially determined by SDS-PAGE electrophoresis, i.e. 31 kDa (cf. FIG. 1). This difference indicates a possible transformation after translation, which would remove a large part of the C-terminal end of the protein.

The translation product of the agaB gene is a protein of 353 amino acids with a calculated molecular weight of 40.680 kDa and with the deduced amino acid sequence SEQ ID No. 4. Analysis of the hydropathy profile shows a very hydrophobic N-terminal segment in a domain of about 20 amino acids. However, no cleavage site exists according to Von Heijne's "(−3,−1)" rule (supra). This segment therefore seems to be non-cleavable. The signal peptide search results obtained from the software PSORT (Nakai's expert system PSORT) (NAKAI & KANEHISA, Proteins, Structure, Function and Genetics 11, 95–110, (1991)) suggest that the protein possesses a non-cleavable N-terminal signal sequence acting as a transmembrane anchor. It should also be noted that the sequence LVFCCALLLGCGD is in perfect agreement with the signature of the N-terminal end of prokaryotic lipoproteins (Prosite PS00013; BAIROCH et al., Nucl. Acids Res. 24, 189–196, (1995)). In this case a cleavage site would be possible between the residues G17 and C18. These results suggest that AgaB could be a lipoprotein located in the internal membrane of the cell.

The ORF which follows the agaB gene codes for a protein which has a significant homology with the DnaJ protein family (OHKI et al., J. Biol. Chem. 261, 1778–1781, (1986)) (FIG. 3B).

EXAMPLE 7
Similarities of Sequence Between the Proteins AgaA and AgaB of C. drobachiensis and with Other β-glycanases The similarities of sequence between the proteins AgaA and AgaB are illustrated in FIG. 4. The protein AgaA has a 44.5% identity and a 65.7% similarity with the protein AgaB. Numerous domains are fairly similar in the primary sequences from Ile110 to Val287 (numbering of the agarase A sequence). In particular, in one of the best conserved units, two glutamic acid residues are present and are separated by 4 amino acids (Glu147 and Glu152 in the AgaA sequence and Glu184 and Glu189 in the AgaB sequence, emboldened in FIG. 4). This organization is characteristic of the catalytic site of family 16 of glycoside hydrolases (HENRISSAT, Biochem. J. 280, 309–316, (1991)).

No similarity of sequence was found with the agarases of the strain Vibrio sp. JT0107 (SUGANO et al., Appl. Environ. Microbiol. 59, 3750–3756, (1993); Biochim. Biophys. Acta 1218, 105–108, (1994)).

Nevertheless, the agarases (AgaA and AgaB) share significant sequence identities with the β-agarases of *Alteromonas atlantica* GenBank M73783 (BELAS et al., J. Bacteriol. 54, 30–37, (1988)) (53.5% and 48% with AgaA and AgaB respectively) and those of *Streptomyces coelicolor* (BUTTNER et al., Mol. Gen. Genet. 209, 101–109, (1987)) (33% with AgaA and AgaB).

These similarities are also demonstrated by means of the HCA (hydrophobic cluster analysis) method (LEMESLE-VARLOOT et al., Biochimie 72, 555–574, (1990)). FIG. 5 illustrates the HCA comparison between the agarases AgaA and AgaB, namely Agar A Cd and Agar B Cd, respectively, in the Figure, and other enzymes of family 16 of glycoside hydrolases, namely the β-agarase of *Alteromonas atlantica* (Agar Aa), the β-agarase of *Streptomyces coecicolor* (Agar Sc), the κ-carrageenase of *C. drobachiensis* (Kap Cd), the laminarinase of *Rhodothernus marinus* (Lam Rm), the lichenase of *Bacillus macerans* (Lich Bm) and the xyloglucan endotransglycosylase of *Arabidopsis thaliana* (XET At).

The two catalytic residues Glu present in the lichenase of *Bacillus macerans* were taken as anchoring points for the HCA comparison, and the sequences were segmented taking the known three-dimensional structure of this lichenase as the reference.

Thirteen segments of different structure (I–XIII) are shown in FIG. 5, segments I, II, IX, X, XI and XIII appearing to be the best conserved. It may be noted that segment VI is specific for the agarases in this family of glycoside hydrolases and that the catalytic site is located in the segment of structure III.

EXAMPLE 8
Substrate Specificities of the Recombinant Agarases AgaA and AgaB

The substrate specificities of the agarases of the invention were studied by analyzing the products resulting from the degradation of neoagarododecaose by the recombinant agarases AgaA and AgaB.

The neoagarododecaose was prepared as follows: Agarose was hydrolyzed with agarase using 0.32 U/mg of polymer. The resistant fraction was precipitated in isopropanol and the soluble oligosaccharides were fractionated by preparative exclusion chromatography on Bio-gel P2 (95 cm×4.4 cm; 25° C.; eluent: distilled water). Detection was effected with an apparatus for recording the differential refractive index (ROCHAS & HEYRAUD, Polymer Bull. 5, 81–86, (1981)). The oligomeric fraction corresponding to the neoagarododecaose was concentrated on a rotary evaporator and lyophilized.

The recombinant clones of *E. coli* containing plasmids pAC1 and pAC4 (with agarase A and agarase B activity, respectively) were cultured for 12 hours at 37° C. in 1 liter of LB medium (Luria-Bertani medium). The cells were centrifuged at 2000 g for 20 minutes, suspended in 30 ml of MES buffer and burst with the aid of a French press at 20,000 psi. After centrifugation at 20,000 g for 1 hour, the cell fragments were discarded and the volume of the supernatant was reduced to 5 ml using an ultrafiltration cell (Amicon, 10 kDa cut-off threshold).

500 µl of each extract obtained in this way were added to 1 ml of neoagarododecaose in MES buffer (50 mg/ml) and the mixtures were incubated at 37° C. for 18 hours. The degree of polymerization of the final products was determined by HPAE chromatography using a pulsed electrochemical detector and an anion exchange column (CarboPAC PA100, Dionex) under the following conditions: flow rate: 1 ml/min; buffer A: 150 mM NaOH; buffer B: 500 mM sodium acetate in 150 mM NaOH; gradient:

0 to 5 min: 70% of A, 30% of B;

5 to 16 min: 40% of A, 60% of B;

16 to 20 min: 100% of B.

The results obtained by HPAE chromatography (high performance anion exchange chromatography) are illustrated in FIGS. 6A to 6C, in which the various abbreviations have the following meanings:

nC: nanocoulomb

DP1: neoagarobiose

DP2: neoagarotetraose

DP3: neoagarohexaose

DP4: neoagarooctaose

DP5: neoagarodecaose

DP6: neoagarododecaose

DP7: neoagarotetradecaose

DP8: neoagarohexadecaose

The final products resulting from the hydrolysis of neoagarododecaose by agarase A and agarase B are shown in FIGS. 6B and 6C respectively. In comparison with neoagarododecaose without enzyme (FIG. 6A), the elution profile after 18 hours of digestion shows neoagarotetraose (DP2) to be the major product and neoagarohexaose (DP3) to be the minor product in both cases (AgaA and AgaB).

What is claimed is:

1. An isolated agaA gene coding for a β-agarase, characterized in that it has SEQ ID No. 1.

2. An isolated agaB gene coding for a β-agarase, characterized in that it has SEQ ID No. 3.

3. An isolated gene according to claim 1, characterized in that it codes for a β-agarase of *Cytophaga drobachiensis* deposited in the DSMZ Collection (Deutsche Sammlung von Mikroorganismen und Zellkulturen GmbH (German Collection of Microorganisms and Cell Cultures)) on May 8, 1998 under the number DSM 12170.

4. An isolated protein AgaA of the β-agarase type from *C. drobachiensis* DSM 12170, characterized in that it has SEQ ID No. 2.

5. An isolated protein AgaB of the β-agarase type from *C. drobachiensis* DSM 12170, characterized in that it has SEQ ID No. 4.

6. An isolated peptide fragment AgaA' of the protein according to claim 4, characterized in that it has SEQ ID No. 6 and β-agarase activity.

7. An isolated nucleic acid having a sequence coding for the protein according to claim 4.

8. An isolated nucleic acid, characterized in that its sequence consists of:

a) the DNA sequence SEQ ID No. 1 coding for the protein AgaA;
 b) a DNA sequence that, because of the degeneracy of the genetic code, is derived from sequence a) above and codes for the protein AgaA; or
 c) an mRNA sequence corresponding to a DNA sequence of a) or b) above.

9. An isolated nucleic acid having a sequence coding for the protein according to claim 5.

10. An isolated nucleic acid, characterized in that its sequence consists of:

a) the DNA sequence SEQ ID No. 3 coding for the protein AgaB;
 b) a DNA sequence that, because of the degeneracy of the genetic code, is derived from sequence a) above and codes for the protein AgaB; or
 c) an mRNA sequence corresponding to a DNA sequence of a) or b) above.

11. An isolated nucleic acid having a sequence coding for the peptide fragment according to claim 6.

12. An isolated nucleic acid characterized in that its sequence consists of:

a) the DNA sequence SEQ ID No. 5 coding for the peptide fragment AgaA';
 b) a DNA sequence that, because of the degeneracy of the genetic code, is derived from sequence a) above and codes for the peptide fragment AgaA'; or
 c) an mRNA sequence corresponding to a DNA sequence of a) or b) above.

13. Expression vector, characterized in that it comprises a nucleic acid sequence according to claim 7 and the means necessary for its expression.

14. Host microorganisms or cells transformed by an expression vector according to claim 13.

15. An isolated gene according to claim 2, characterized in that it codes for a β-agarase of *Cytophaga drobachiensis* deposited in the DSMZ Collection (Deutsche Sammlung von Mikroorganismen und Zellkulturen GmbH (German Collection of Microorganisms and Cell Cultures)) on May 8, 1998 under the number DSM 12170.

16. An expression vector, characterized in that it comprises a nucleic acid sequence according to claim 9 and the means necessary for its expression.

17. A host microorganism or cell transformed by an expression vector according to claim 16.

* * * * *